(12) United States Patent
Hiereth et al.

(10) Patent No.: US 9,393,081 B2
(45) Date of Patent: Jul. 19, 2016

(54) LIGHT GUIDE UNIT FOR A LASER APPLICATOR

(75) Inventors: Werner Hiereth, Gilching (DE);
Thomas Kreitmaier, Schwabhausen (DE); Oliver Durian, Bobingen (DE)

(73) Assignee: DORNIER MEDTECH LASER GMBH, Wessling (DE)

( * ) Notice: Subject to any disclaimer, the term of this patent is extended or adjusted under 35 U.S.C. 154(b) by 176 days.

(21) Appl. No.: 13/297,593

(22) Filed: Nov. 16, 2011

(65) Prior Publication Data

US 2012/0123398 A1      May 17, 2012

(30) Foreign Application Priority Data

Nov. 17, 2010   (EP) .................................... 10014710

(51) Int. Cl.
*A61B 18/20* (2006.01)
*A61C 1/00* (2006.01)
*G02B 6/38* (2006.01)
*A61B 18/22* (2006.01)
*A61B 18/24* (2006.01)
*A61B 18/00* (2006.01)

(52) U.S. Cl.
CPC ............... *A61C 1/0046* (2013.01); *A61B 18/22* (2013.01); *G02B 6/38* (2013.01); *A61B 18/24* (2013.01); *A61B 2018/0091* (2013.01)

(58) Field of Classification Search
CPC .................................. A61B 18/20; G02B 6/38
See application file for complete search history.

(56) References Cited

U.S. PATENT DOCUMENTS

| 5,129,896 A | * | 7/1992 | Hasson .......................... 606/15 |
| 5,796,895 A | * | 8/1998 | Jennings et al. ................. 385/56 |
| 6,540,414 B1 | * | 4/2003 | Brezina et al. ................... 385/92 |
| 2004/0114879 A1 | * | 6/2004 | Hiereth et al. ................... 385/88 |

FOREIGN PATENT DOCUMENTS

| DE | EP 0507991 A2 * 11/1991 ..................... 385/15 |
| DE | 198 55 438         6/1999 |
| DE | 10 2009 000685    8/2010 |

OTHER PUBLICATIONS

European Search Report for EP Application No. 10014710; issued on Apr. 14, 2011.

* cited by examiner

*Primary Examiner* — Lynsey Crandall
(74) *Attorney, Agent, or Firm* — King & Spalding LLP (57) ABSTRACT

The present invention relates to a light guide unit for a laser applicator, wherein the light guide unit has a light guide tip assembly removably insertable into the laser applicator, wherein the light guide tip assembly comprises an optical fiber and a coupling member provided on a proximal end of the optical fiber. When the coupling member is provided on the optical fiber, a proximal end face of the optical fiber needs to be kept clean. It is also desired that the light guide tip assembly can be manufactured easily. It is suggested to provide the coupling member via a casting technique.

17 Claims, 7 Drawing Sheets

LIGHT GUIDE UNIT FOR A LASER APPLICATOR

CROSS-REFERENCE TO RELATED APPLICATIONS

This application claims priority to European Patent Application No. 10014710.7 filed Nov. 17, 2010, the contents of which is hereby incorporated in its entirety by reference.

DISCLOSURE

The present invention relates to a light guide unit for a laser applicator, in particular for a medical laser applicator, wherein the light guide unit comprises the features of the preamble of claim 1. DE 198 55 438 A1 relates to a medical laser applicator in form of a handpiece for a dentist, the applicator having a generic light guide unit. An optical fiber is removably insertable into the handpiece. A coupling bushing is provided at a proximal end of the optical fiber. The coupling bushing is fixed to the fiber by gluing.

The optical fiber has a proximal end face that extends across to the longitudinal direction of the optical fiber and into which the laser light needed at a distal end of the optical fiber enters the optical fiber. The gluing technique makes it possible to fix the coupling bushing on the proximal end of the optical fiber without making said proximal end face dirty so that difficult cleaning work is not necessary. The proximal end face of the optical fiber must not be damaged during such a cleaning.

Other fixing techniques, bearing the risk that the proximal end of the optical fiber might become dirty, are prevented. Another possibility for fixing a coupling bushing to an optical fiber in a clean manner is mechanically clamping the coupling bushing onto the fiber. Also here, the proximal end face of the optical fiber is kept clean and it is even possible to readjust the relative position of optical fiber and coupling bushing if the clamping mechanism is releasable.

DE 10 2009 000 685 A1 discloses a medical handpiece for a dentist in which a coupling bushing is mechanically fixed onto an optical fiber. In order to avoid damaging the optical fiber during the mechanical clamping action, it is suggested to use a sleeve for protecting the optical fiber during this work. This sleeve can also be used as a protective shield when the optical fiber is transported, and it is usable as a tool for inserting and mounting the optical fiber into the handpiece. After the optical fiber has been inserted, the sleeve is removed.

It is the object of the present invention to provide a generic light guide unit having a light guide tip assembly that is easy to manufacture but also has good optical properties.

According to the present invention, the object is solved with a light guide unit having the features of claim 1. Surprisingly, it is possible to obtain a light guide tip assembly with good optical properties by providing the proximal coupling member to the optical fiber by casting, in particular by injection molding. It was expected that the liquid material for forming the proximal coupling member would reach portions of the optical fiber that are not intended to be covered by this material, in particular the proximal end face of the optical fiber. As a cleaning action of the optical fiber, in particular of the proximal end face of the optical fiber, is not necessary, the manufacture of the light guide tip assembly remains easy.

Preferably, the light guide tip assembly might be sterilized. Thus, it can be used with a medical laser applicator, which was sterilized separately, e.g. under more extreme conditions than recommendable for the light guide tip assembly.

Advantageously, the proximal coupling member may comprise a proximal connector that can be connected to a corresponding distal connector of a transmission light guide assembly through which light might be transmitted to and/or from the light guide tip assembly. By means of the proximal connector, a good optical connection can be made between the light guide tip assembly and the transmission light guide assembly.

Favourably, the proximal coupling member might have a fixing portion by means of which the proximal coupling member can be fixed to an applicator adapter. The fixing portion provides for a good fixation of the proximal coupling member to the applicator adapter so as to maintain a relative position between both. The applicator adapter serves for fixing the light guide tip assembly to the laser applicator.

Particularly advantageous, the light guide unit might further comprise a tube that at least partially accommodates the light guide tip assembly. The tube serves as a protective shield surrounding the light guide tip assembly at least partially.

Particularly favourable, the tube and the light guide tip assembly might be movable relative to one another between a first relative position in which the proximal coupling member might be located at a proximal end of the tube, and a second relative position in which the proximal coupling member is located closer to a distal end of the tube, or even at the distal end of the tube. Especially, the tube can be partially pulled beyond the light guide tip assembly. In the case the proximal coupling member is connected to a transmission light guide assembly and the tube is capable of accommodating at least a distal portion of the transmission light guide assembly, the tube is a protective shield at least partially surrounding the transmission light guide assembly in said second relative position.

Particularly preferable, the tube might be sterilized. Due to the sterilization, and if the tube is in said second relative position and at least partially surrounds the transmission light guide assembly, the tube provides a sterile shield around the transmission light guide assembly, so that a sterile outside surface is provided here, even if the transmission light guide assembly is not sterilized.

Advantageously, the tube might have a securing section by means of which it can be secured to a corresponding securing section of an applicator adapter. By means of its securing section, the tube can be securely held on the applicator adapter and a relative position of the tube to the applicator adapter can be maintained.

Particularly advantageous, the tube might have inner dimensions corresponding to maximum outer dimensions of a proximal connector of the proximal coupling member in a connected or disconnected state, the maximum outer dimensions of the proximal connector increasing during a connecting and/or disconnecting action. Hereby, the tube blocks a connecting or disconnecting action. Thus, it secures a connection of the proximal connector with a corresponding distal connector.

Preferably, the light guide unit might further comprise an applicator adapter by means of which the light guide tip assembly can be secured to the laser applicator. The applicator adapter might comprise an applicator attachment element by means of which the applicator connector can be secured to the laser applicator, and might further comprise a fixing portion by means of which the proximal coupling member of the light guide tip assembly can be fixed to the applicator adapter, and/or a clamp mechanism by means of which a transmission light guide assembly, through which light is transmittable to and/or from the light guide tip assembly, can be secured to the applicator adapter. Thus, the light guide tip assembly and/or the transmission light guide assembly can be secured to the laser applicator by means of the applicator adapter. If the fixing portion is provided, the light guide tip assembly can be fixed to the applicator adapter directly. If the clamp mechanism is provided and the light guide tip assembly is mechanically fixed to the transmission light guide assembly, the light guide tip assembly is fixed to the applicator adapter indirectly via the transmission light guide assembly.

In a modification, the light guide unit could be provided in a version not comprising the light guide tip assembly, the transmission light guide assembly and tube (as discussed later). That is, the light guide unit could comprise the applicator adapter alone.

Particularly preferable, the applicator adapter might comprise a pipe that can accommodate the proximal coupling member of the light guide tip assembly. The pipe is a protective shield surrounding the proximal coupling member.

Particularly favourable, the applicator adapter might comprise a pipe that can accommodate a portion of the above-mentioned tube. Accordingly, the pipe is a protective shield surrounding said portion of the tube.

Advantageously, the tube might be at least partially positioned between the pipe and the fixing portion. Thus, the tube can be arranged in a space efficient manner.

Preferably, the clamp mechanism may comprise male and female cone members that are varying an inner space of the clamp mechanism when moving axially relative to one another. Hereby, the cone members are varying the inner space and applying a corresponding clamping force in a gear-like manner.

Particularly favourable, the applicator adapter may have a pipe with at least one of the features mentioned above, wherein a portion of the pipe may belong to the clamp mechanism. This makes it possible to provide a construction with a reduced number of parts, as at least one function of the clamp mechanism is fulfilled by the pipe.

Favourably, said portion of the pipe may comprise one of the cone members. This means that the pipe is used for realizing a gear and/or a clamp function.

Advantageously, said portion of the pipe may comprise a part of an adjustment drive mechanism, wherein the axial relative position of the cone members can be adjusted by means of the adjustment drive mechanism. By using said portion of the pipe as a part of the adjustment drive mechanism, a construction with a reduced number of parts can be realized.

Preferably, the applicator adapter may be sterilized. This provides for a larger sterile area, even if no sterile tube is used.

In a modification, it is possible to provide a light guide unit having the features of claim 1 except for the feature that the proximal coupling member is cast, and this light guide unit may additionally have one or more of the above-mentioned features of the present invention and/or one or more of the below mentioned further features of the present invention.

In the following, a light guide unit 100 of a first embodiment of the present invention is explained.

Figure 1:
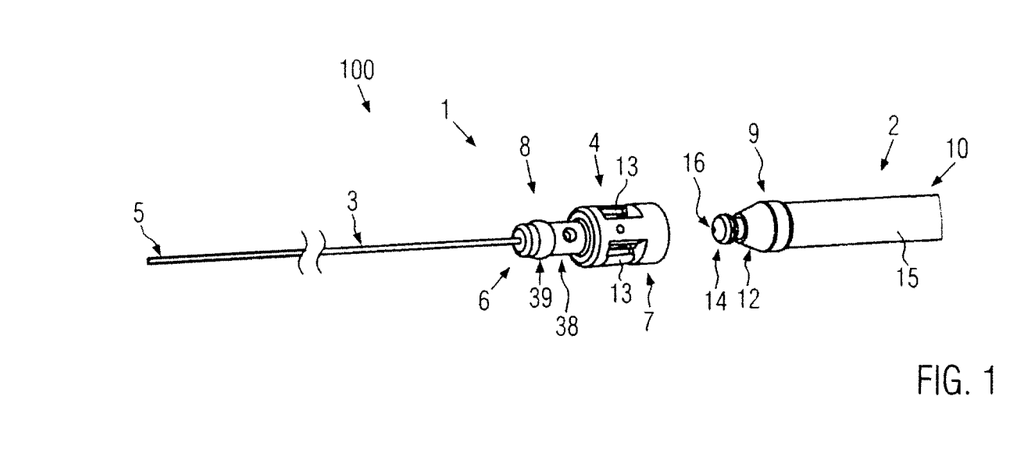
FIG. 1: is a perspective view of a partially shown light guide tip assembly and a partially transmission light guide assembly of a light guide unit of a first embodiment of the present invention in a separated state.

The light guide unit 100 comprises a light guide tip assembly 1 and a transmission light guide assembly 2, shown in a separated state in FIG. 1. The light guide tip assembly 1 comprises an optical fiber 3, which is only partially shown, and a proximal coupling member 4. The optical fiber 3 has an application end 5 and a proximal end 6. The proximal coupling member 4 is cast, preferably injection molded, onto the proximal end 6 of optical fiber 3, preferably with the optical fiber being inserted in the mold. The optical fiber 3 may comprise a fiber core surrounded by a coating, e.g. polyamide coating. In this case, the proximal coupling member 4 is cast, in particular injected molded, onto the coating on the proximal end 6 of the optical fiber 3. The proximal coupling member 4 can be made from plastic material, which preferably bonds mechanically, chemically, physically and/or thermically to the optical fiber in the course of the casting process, in particular to said coating, if provided. For instance, the proximal coupling member can be made from a liquid crystal polymer.

The optical fiber 3 of the light guide tip assembly 1 can preferably be cleaved, most preferably laser cleaved, and the application end of the fiber might preferably be rounded by a laser cleaving process. In some applications or treatments, the application end 5 of the optical fiber 3 might be brought into direct contact with the area to be treated, e.g. a body part or tissue of a patient. The optical fiber 3 might have a length in the range from 20 to 1000 mm. In some cases, the optical fiber 3 might extend beyond the laser applicator, e.g. handpiece, into and through which the optical fiber 3 of the light guide tip assembly 1 is inserted.

The optical fiber 3 of the light guide tip assembly 1 might be a silica fiber having a numerical aperture of 0.37 or lower, most preferably of 0.22 or lower. The optical fiber 3 of the light guide tip assembly 1 might have a core diameter of 50 to 400 µm, most preferably of 100 to 200 µm. The proximal coupling member 4 has, on a proximal side, a proximal connector 7, and at a distal side, a fixing portion 8. The proximal connector 7 and the fixing portion 8 are integrally formed. The fixing portion has smaller outside dimensions than the proximal connector and will be described later.

The proximal connector 7 is mechanically and releasably connectable to a corresponding distal connector 9 provided on a distal end 10 of the transmission light guide assembly 2. In the present embodiment, the proximal connector 7 is a socket, and the distal connector 9 is a plug. Alternatively, the proximal connector can be a plug and the distal connector can be a socket. The proximal connector 7 has an inner cone section 11 and the distal connector 9 has a corresponding outer cone section 12. The cone sections 11, 12 serve to center and align both connectors 7, 9 when they are connected.

Figure 3:
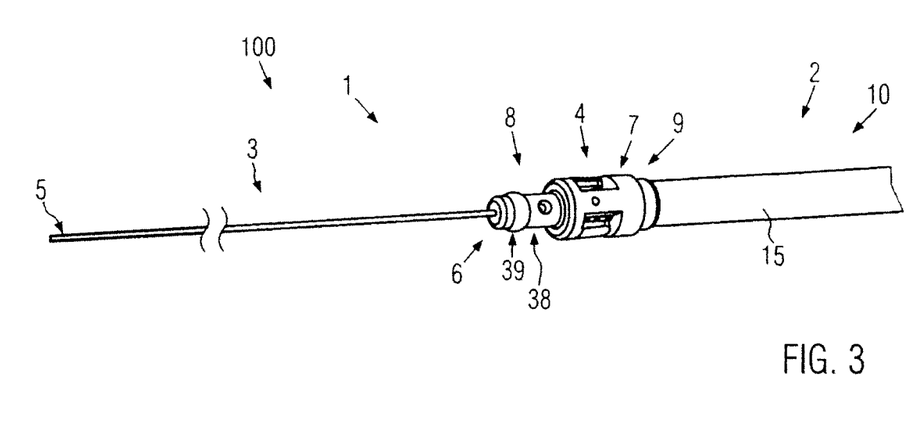
Figure 4:
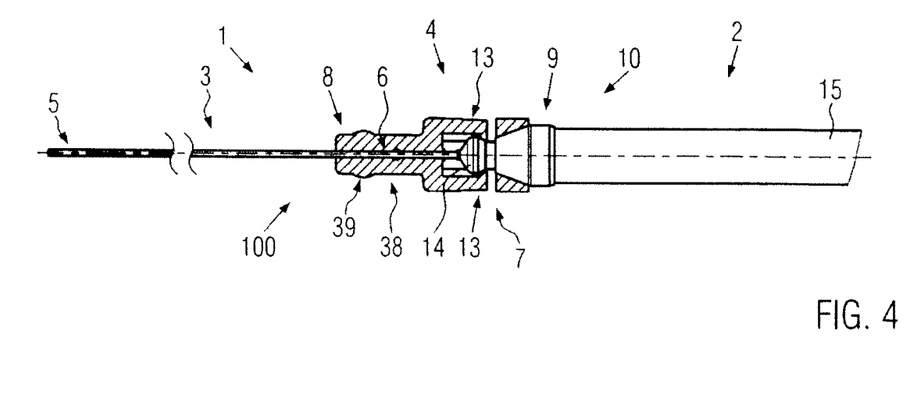
FIG. 4: is a longitudinal sectional view of the light guide tip assembly and a side view of the transmission light guide assembly of FIG. 3, FIG. 5: is a longitudinal sectional view of a tube assembly, wherein the light guide tip assembly of FIGS. 1 and 2 and a tube are in a first relative position.

The proximal connector 7 has flexible hooks 13 for sliding over a cam profile 14 of the distal connector. Thus, both connectors are releasably securable to one another by a latch mechanism. FIGS. 3 and 4 show the light guide tip assembly 1 and the transmission light guide assembly 2 in a connected state. The light guide tip assembly is shown in a longitudinal sectional view in FIG. 4 and it is clearly visible how the flexible hooks engage a proximal side of the cam profile 14 of the distal connector 9.

The maximum outer dimensions, in particular the maximum outer width or diameter, of the proximal connector is in a normal state when the proximal connector 7 is connected to or disconnected from the distal connector 9. During a connecting or disconnecting action, the maximum outer dimension of the proximal connector 7 increases because the flexible hooks 13 are pivoting outwardly when they slide over the cam profile 14.

Figure 2:
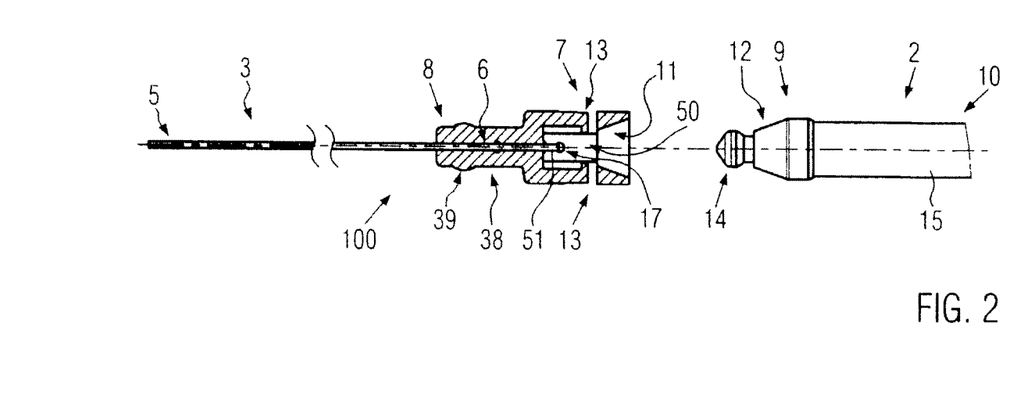
FIG. 2: is a longitudinal sectional view of the light guide tip assembly and a side view of the transmission light guide assembly of FIG. 1, FIG. 3: is a perspective view of the light guide tip assembly and the transmission light guide assembly of FIGS. 1 and 2 in a connected state.

The transmission light guide assembly 2 has an optical transmission cable 15 on whose distal end the distal connector 9 is provided. The transmission light guide assembly 2 might have a length in the range from 1 to 12 m, preferably in the range from 2 to 3 m. Inside the cable, which might incorporate a metal tube, an optical fiber 23 (shown in FIG. 6) is provided. This optical fiber might have a core diameter in the range from 10 to 300 µm, preferably in the range from 50 to 200 µm. Said optical fiber 23 has a distal end face 16 that is flush with the distal end of the distal connector 9, as best shown in FIG. 1. This distal end face 16 abuts against a proximal end face 17 of the optical fiber 3 of the light guide tip assembly 1 when both connectors are in a connected state, as best shown in FIG. 4. The proximal end face 17 of the optical fiber 3 of the light guide tip assembly 1 belongs to an end section 51 of the proximal end 6 of this optical fiber 3, and said end section 51 projects into a cavity 50 of the proximal connector, as shown in FIG. 2.

At least a part of the light guide tip assembly 1, in particular of its optical fiber 3, is removably insertable into a laser applicator, which can be a medical laser applicator such as a handpiece. It might be necessary for an application or treatment that the light guide tip assembly be provided in a sterile state. As the proximal coupling member 4 is provided on the optical fiber by a casting technique in which the proximal end face of the optical fiber is kept clean, the light guide tip assembly can be produced in an easy manner, which means low manufacturing costs. Thus, the light guide tip assembly can be disposed after being used and a new sterile light guide tip assembly 1 can be taken for the next application or treatment. The transmission light guide assembly 2 can be reused.

The coupling realized between the light guide tip assembly 1 and the transmission light guide assembly 2 is a fiber-fiber coupling, i.e. a coupling that does not require an imaging optical device. As an imaging optical device is not needed, a higher precision is required when coupling both optical fibers 3, 23 with one another. The physical limit for coupling two optical end faces in air (without anti-reflex coating) is 92%. Thus, for achieving a reliable fiber-fiber coupling, usually a 400 µm fiber is coupled into a 600 µm fiber or a 200 µm fiber is coupled into a 400 µm fiber.

With the present invention, it is possible to achieve such a high precision with the above-described casting technique that the difference of the core diameter of both fibers can be at least reduced by 100 µm, e.g. a 200 µm fiber can be coupled into a 300 µm fiber, and it is even possible to couple a 200 µm fiber into a 220 µm fiber. These results are achieved with high production quality. For instance, 300 samples of a coupling in which a 200 µm fiber that is coupled into a 300 µm fiber have been produced without one defective fiber-fiber coupling. This means further that it is possible to realize a production that requires only a reduced effort for quality testing.

The light guide unit 100 further comprises a flexible tube 18, which can at least partially accommodate the light guide tip assembly 1. The light guide tip assembly 1 and the tube 18 together constitute a tube assembly 19. The light guide tip assembly 1 is movably provided within and held by the tube 18 over a substantial length of the tube 18. The maximum outer dimensions of proximal connector 7 correspond in their normal state to the inner dimensions of the tube 18 provided over a substantial length of the tube 18. An interference fit is provided in which the axial relative positions of the proximal coupling member 4 and the tube 18 can be securely maintained, but it is still possible to move the light guide tip assembly 1 axially inside the tube 18 easily or with moderate force.

Figure 5:
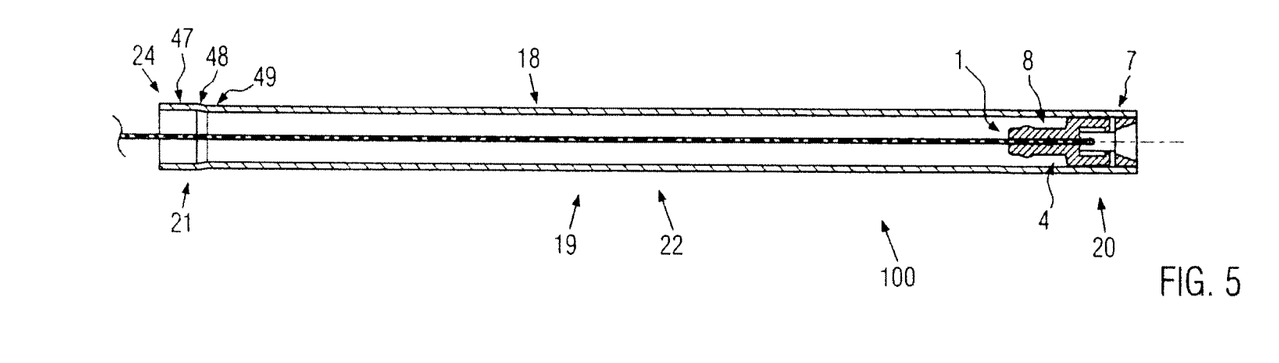

FIG. 5 shows the tube 18 and the light guide tip assembly 1 in a first relative position in which the proximal coupling member 4 is located at a proximal end 20 of the tube 18 inside the tube 18. This can be the state in which the tube assembly 19 is delivered to a customer.

Figure 6:
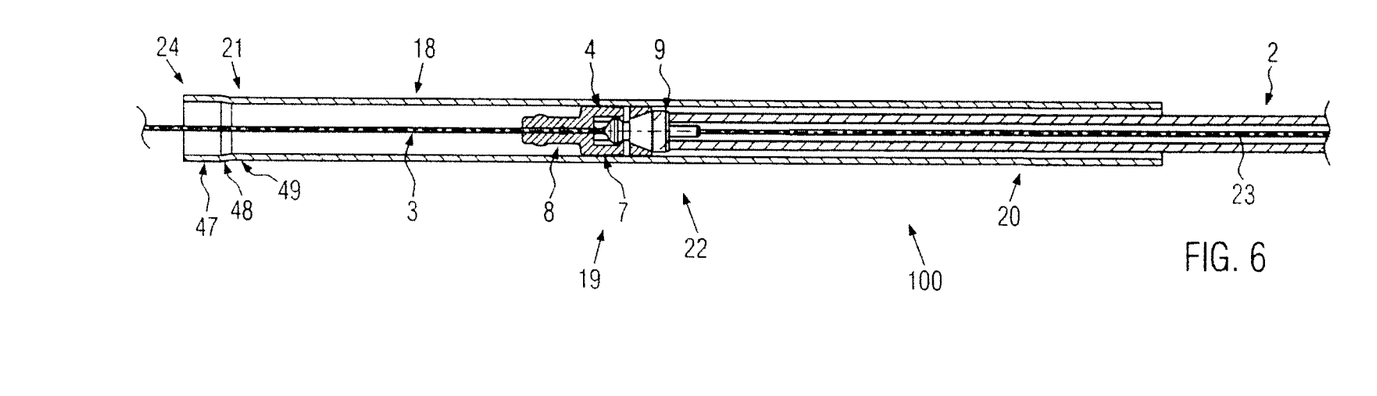
FIG. 6: is a longitudinal sectional view of the tube assembly in which the tube and the light guide tip assembly are in a second relative position and in which the light guide tip assembly is connected to the transmission light guide assembly of FIGS. 1 to 4, the transmission light guide assembly being partially shown in a longitudinal sectional view.

The light guide tip assembly 1 and the tube 18 are movable to a second relative position in which the proximal coupling member 4 is located closer to a distal end of the tube 18 (for example, as shown in FIG. 6), or even at the distal end 21 of the tube 18 inside the tube (not shown in FIG. 6). In FIG. 6, tube 18 and the light guide tip assembly 1 are in a relative position in which the proximal coupling member 4 is positioned in a middle portion 22 of the tube 18. In the depiction of FIG. 6, the transmission light guide assembly 2 is connected to the proximal coupling member 4, wherein the transmission light guide assembly 2 extends for a corresponding distance inside the tube 18. FIG. 6 shows most of the parts in a longitudinal sectional view, so that also the optical fiber 23 of the transmission light guide assembly 2 is visible.

The distal connector 9 of the transmission light guide assembly 2 can be connected to the proximal connector 7 of the light guide tip assembly 1 while the proximal connector 7 is at least partially positioned outside the tube 18 so that the flexible fingers 13 may sufficiently pivot outwardly. Thereafter, the light guide tip assembly 1, in particular the proximal coupling member 4, can be moved into and inside the tube 18 towards the distal end 20 of same with the help of the transmission light guide assembly 2. The tube 18 secures both connectors in their connected state as the flexible fingers 13 are prevented from pivoting too far outwardly.

The tube 18 can be provided in a sterilized state. If the transmission light guide assembly 2 is inserted into the tube 18, the tube 18 becomes a shield surrounding the inserted portion of the transmission light guide assembly 2. Thus, the sterile area provided by the tube 18 is extended over this portion of the transmission light guide assembly 2. If, for instance, the tube 18 and the light guide tip assembly 1 are provided in a sterile state but the transmission light guide assembly 2 is not sterile, the sterile area provided by the tube 18 and the light guide tip assembly 1 can be prolonged by pulling the tube 18 over the transmission light guide assembly 2. This aspect is independent from the feature that the proximal coupling member 4 is cast onto the optical fiber 3. An end portion of the distal end 21 of the tube 18 comprises a securing section 24. The securing section 24 comprises a normal diameter part 49 that has the same diameter as the rest of the tube 18, an increased diameter part 47, whose diameter is increased with respect to the diameter of the rest of the tube 18, and a flat step 48 between the increased diameter part 47 and the normal diameter part 49.

In a variation of the present invention, the tube can be longer than the fiber tip assembly 1. Thus, the tube 18 would still surround the complete fiber tip assembly 1 even if it is pulled over a part of the transmission light guide assembly 2. This means further that a sterile area can be provided around the transmission light guide assembly 2, which sterile area is longer than the fiber tip assembly.

Further, the tube could be provided in combination with a sheath or catheter. For instance, the sheath or catheter could be provided surrounding the optical fiber 3 of the light guide tip assembly 1 and could extend beyond the application end 5 of the optical fiber 3. In the first relative position of the proximal coupling member and the tube, the tube could, for instance, terminate approximately where the catheter/sheath terminates (distal end). By bringing the tube and the proximal coupling member into their second relative position, the assembly incorporating the catheter/sheath is made ready for use.

It would even be possible to provide the distal end of the tube as a catheter/sheath so that no further catheter or sheath surrounding the optical fiber 3 of the light guide tip assembly 1 is necessary.

The light guide unit 100 further comprises an applicator adapter 25 by means of which the light guide tip assembly 1 can be directly or indirectly secured to the laser applicator 28, shown in phantom lines in FIGS. 7 to 10. The applicator adapter 25 comprises a main part 26 and a pipe 27. The main part 26 and the pipe 27 are separate elements, as becomes clear from the exploded view of FIGS. 7 and 8.

The main part 26 comprises an applicator attachment element 29 by means of which the applicator adapter 25 can be secured to the laser applicator 28, in particular to a corresponding adapter attachment element 30 of the laser applicator 28. The applicator attachment element 29 comprises a cylindrical portion 31 with an internal thread 32 fitting to a corresponding external thread 33 of the adapter attachment element 30. Radially outside to the cylindrical portion 31, a handling profile 34 is provided on the main part 26.

The main part 26 further comprises a multi attachment member 35. The multi attachment member 35 comprises a cylindrical section 36, the inside of which comprises a fixing portion 37 by means of which the proximal coupling member 4 can be fixed to the applicator adapter 25. In particular, the fixing portion 8 of the proximal coupling member 4 is inserted into the fixing portion 37 of the multi attachment member 35. The fixing portion 8 of the proximal coupling member 4 has a smaller maximum diameter than the proximal connector 7. The fixing portion 8 of the proximal coupling member 4 has a rod-like member 38 of basically round cross-sectional profile, on which rod-like member 38 a ring-like projection 39 is provided, as best shown in FIGS. 1 and 2. The ring-like projection 39 provides for an interference fit between both fixing portions 8, 37 so that the proximal coupling member 4 is securely held on the main part 26 of the applicator adapter 25.

Figure 7:
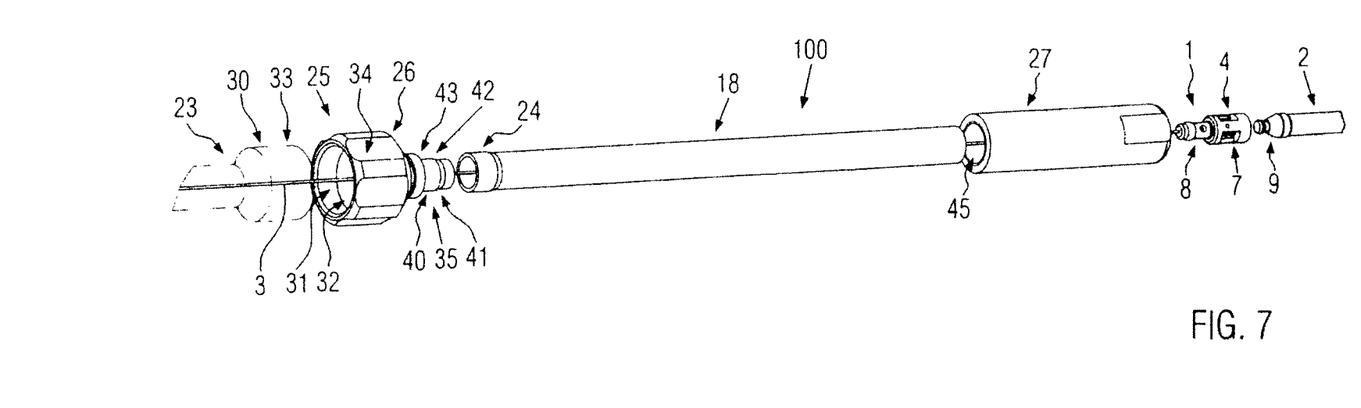
FIG. 7: is an exploded perspective view of the light guide tip assembly, the transmission light guide assembly, a tube and an applicator adapter.
Figure 8:
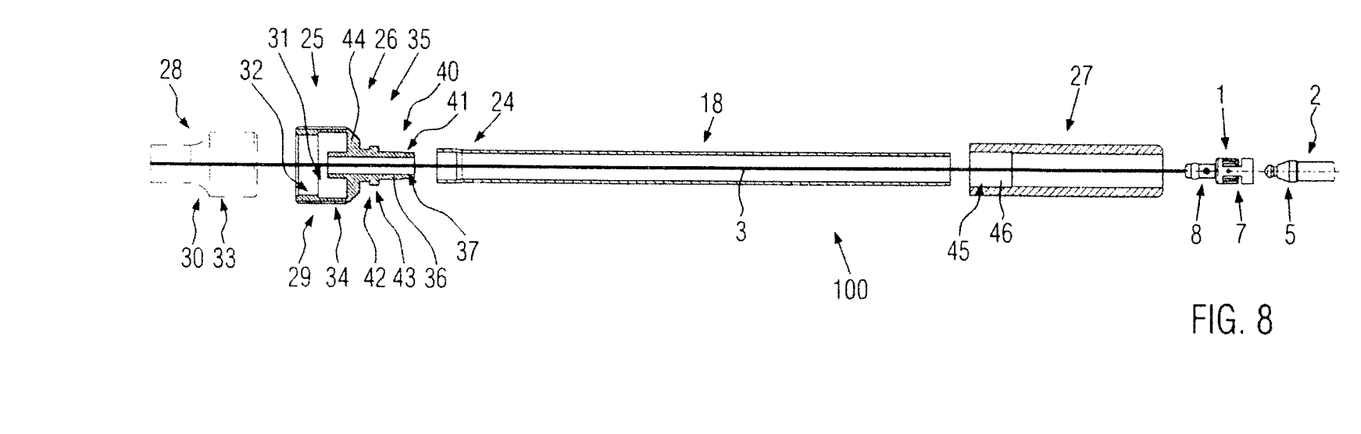
FIG. 8: is an exploded view of the elements of FIG. 7, wherein the applicator adapter and the tube are shown in a longitudinal sectional view, and the light guide tip assembly and the transmission light guide assembly in a side view.

A securing section 40 is provided on the outside of the proximal end of the cylindrical section 36 of the multi attachment member 35. The securing section 40 has an outer profile corresponding to the inner profile of the securing section 24 of the tube 18. Thus, the outer diameter of the securing section 40 of the multi attachment member 35 reduces at a flat step 41, seen in the proximal direction, as shown in FIGS. 7 and 8.

The multi attachment member 35 further comprises a fastening portion 42 provided between the securing section 40 and the applicator attachment element 29 of the main part 26. The fastening portion 42 comprises an external thread 43 and terminates with a radially extending abutment wall 44. The abutment wall 44 is also a part of the applicator attachment element 29, namely a proximal end face of the adapter attachment element 30 may abut against the abutment wall 44. The fastening portion 42 of the multi attachment member 35 has an external thread 43 and corresponds to a fastening portion 45 provided at a distal end of the pipe 27, wherein the fastening portion 45 of the pipe 27 has an internal thread 46.

Figure 9:
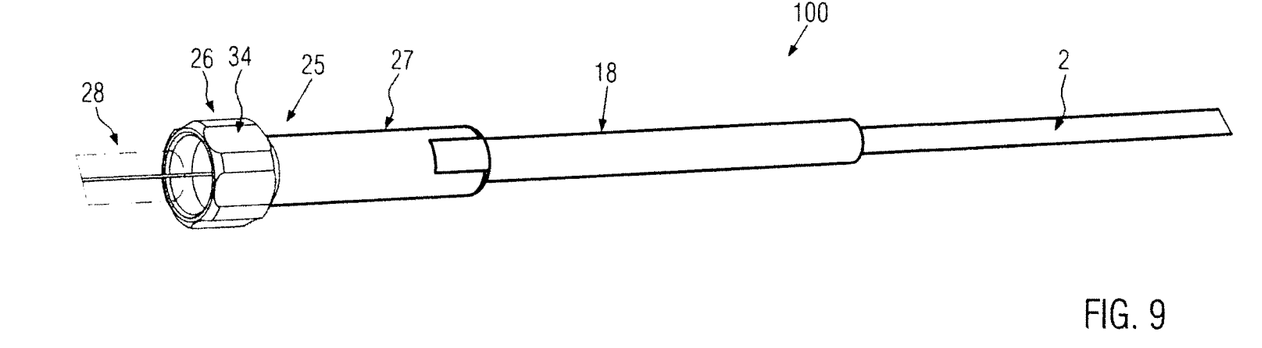
FIG. 9: is a perspective view of the light guide tip assembly, the transmission light guide assembly, the tube and the applicator adapter in a partially assembled state.
Figure 10:
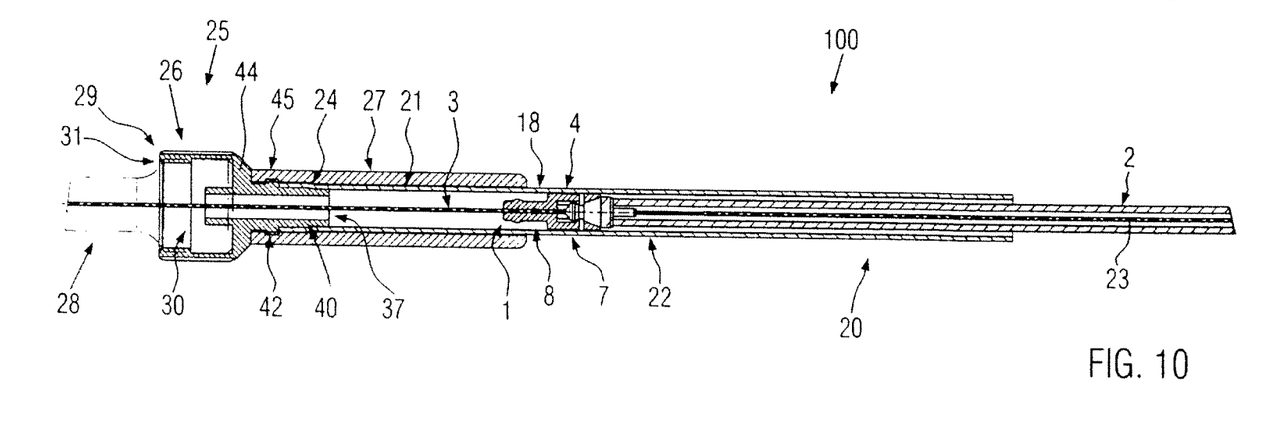
FIG. 10: is a longitudinal sectional view of the light guide tip assembly, a part of the transmission light guide assembly, the tube and the applicator adapter of FIG. 9, FIG. 11: relates to a light guide unit of a second embodiment of the present invention and shows a light guide tip assembly, a transmission light guide assembly and an applicator adapter in a perspective, partially exploded view.

In the perspective views of FIGS. 9 and 10, the tube 18 is shown secured to the multi attachment member 35 with both securing sections 24, 40 being in engagement with one another. The pipe 27 of the applicator adapter 25 accommodates a part of the tube 18 and is fastened to the main part 26. Also, the applicator attachment element 29 of the applicator adapter 25 is attached to the adapter attachment element 30 of the laser applicator 28.

In the depiction of FIGS. 9 and 10, the light guide tip assembly 1 and the transmission light guide assembly 2 are connected to one another, wherein the proximal coupling member 4 is positioned in the middle portion 22 of the tube 18, but the fixing portion 8 of the proximal coupling member 4 has not yet been inserted into the fixing portion 37 of the multi attachment member 35. Herefor, the transmission light guide assembly 2 has to be pushed further into the tube 18 so as to bring the two fixing portions 8, 37 into fixing engagement with one another.

As also becomes clear from FIG. 10, the pipe 27 of the applicator adapter 25 can accommodate the proximal coupling member 4 of the light guide tip assembly 1. Moreover, the proximal coupling member 4 can even be securely fixed to the applicator adapter 25 while the tube 18 could be omitted. If the tube 18 is omitted and the applicator adapter 25 is provided in a sterile state, also a sterile element, namely the pipe 27, would surround a portion of the transmission light guide assembly 2 in a shielding manner.

The applicator adapter 25, the tube 18 and the light guide tip assembly 1 might be delivered to a customer together in a sterilized state.

The applicator adapter 25 and the transmission light guide assembly 2 together constitute an adapter assembly. The tube 18 might belong to the adapter assembly.

Figure 11:
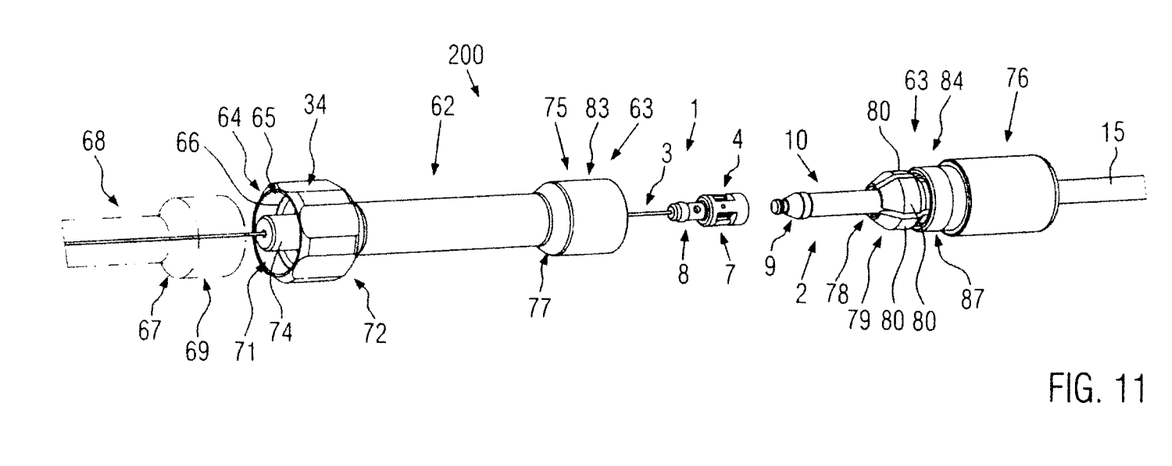
Figure 12:
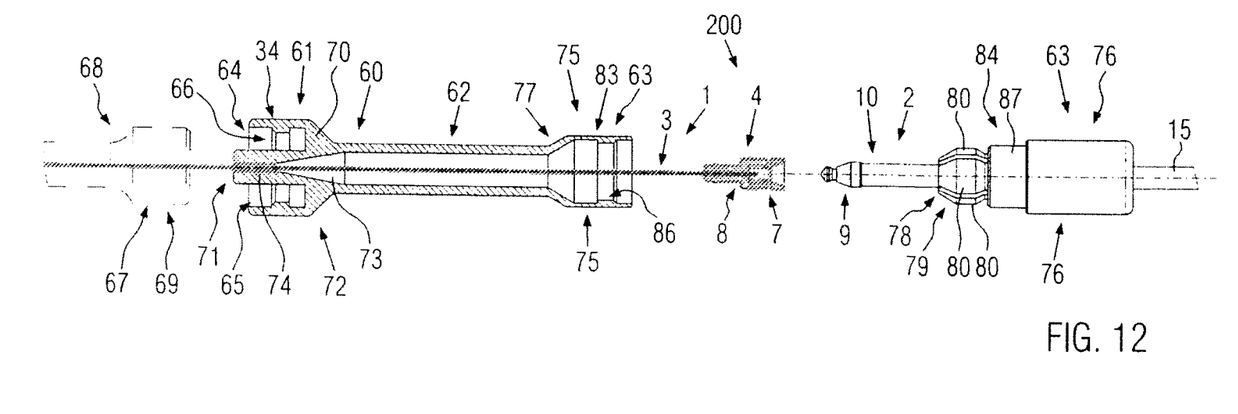
FIG. 12: is an exploded view of the elements of FIG. 11, wherein the light guide tip assembly and a part of the applicator adapter are shown in a longitudinal cross-sectional view and the transmission light guide assembly and a further part of the applicator adapter are shown in a side view.
Figure 13:
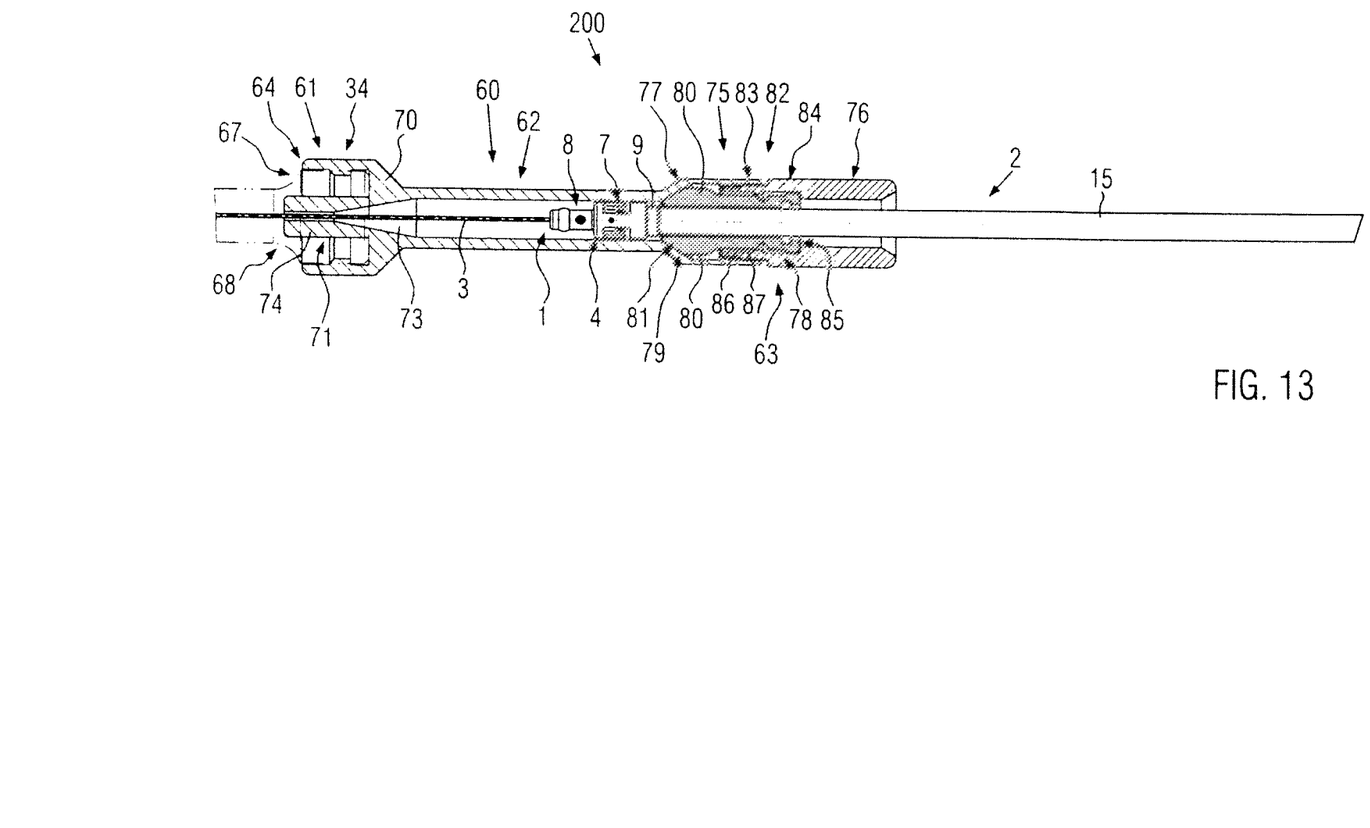
FIG. 13: shows the elements of FIGS. 11 and 12 in an assembled state, wherein the light guide tip assembly and the transmission light guide assembly are shown in a side view, and the applicator adapter is shown in a longitudinal sectional view.

FIGS. 11 through 13 show a light guide unit 200 of a second embodiment of the present invention. In the following, only the differences from the first embodiment are described, and the same reference numerals are used for the same parts.

The second embodiment comprises an applicator adapter 60 that is different from the applicator adapter 25 of the first embodiment. The applicator adapter 60 of the second embodiment comprises a main part 61, a pipe 62 and a clamp mechanism 63, wherein a section of the pipe 62 is a part of the clamp mechanism 63.

The main part 61 comprises an applicator attachment element 64, which has a cylindrical portion 65 with an internal thread 66. The applicator attachment element 64 corresponds to an adapter attachment element 67 of a laser applicator 68, wherein the adapter attachment element 67 has an external thread 69. The applicator attachment element 64 further comprises an abutment wall 70 to which the adapter attachment element 67 may abut. Radially outside to the applicator attachment element 64, the same handling profile 34 as in the first embodiment is provided.

The applicator adapter 60 comprises a fiber guide 71 for centering the optical fiber 3 of the light guide tip assembly 1 when this optical fiber 3 is inserted into and pushed through the applicator adapter 60. The fiber guide 71 is provided at a distal end of the applicator adapter 60 and is coincident with the middle axis of the applicator adapter 60. The fiber guide 71 comprises a cone-like centering section 73, which guides the application end 5 of the optical fiber 3 towards the center of the applicator adapter 60. Subsequent to the centering section 73, seen in the distal direction, a holding portion 74 of the fiber guide 71 is provided, wherein the internal diameter of the holding portion 74 is identical to the minimum inner diameter of the centering section 73. The pipe 62 and the main part 61 are integrally formed in the second embodiment, but they may also be provided as separate parts.

The clamp mechanism comprises a first sleeve 75 and a second sleeve 76. The first sleeve 75 is an end part of the pipe 62, but could also be provided as a separate part to the pipe 62. The first sleeve 75 incorporates a first cone member 77, which cooperates with a second cone member 78 located inside the first and second sleeves 75, 76. The first cone member 77 is a female cone member accommodating at least a portion of the second cone member 78, which is a male cone member. The first cone member 77 is a cone-like increase of the diameter of the pipe 62, and the second cone member 78 comprises a leading, corresponding cone section 79. The second cone member 78 further comprises flexible clamp fingers 80, which are moved radially inwardly if the first and second cone members 77, 78 are moved axially towards one another. The flexible clamp fingers are incorporating the leading cone section 79 at their leading ends, which means that the flexible clamp fingers 80 are varying an inner space 81 surrounded by them if they are in engagement with the first cone member 77 and are axially moved towards or away from the first cone member 77.

The clamp mechanism 63 further comprises an adjustment drive mechanism 82 that adjusts the relative position of the cone members 77, 78. The adjustment drive mechanism 82 comprises a first gear member 83, which is coupled to the first sleeve 75, and a second gear member 84, which is coupled to the second sleeve 76, wherein the second sleeve 76 abuttingly engages a rear face 85 of the second cone member 78, as best shown in FIG. 13. In the present embodiment, the first gear member 83 is part of the first sleeve 75 and comprises an internal thread 86, and the second gear member 84 is part of the second sleeve 76 and comprises an external thread 87. By threading the gear members 83, 84 towards and away from one another, the axial position of the cone members 77, 78 is varied and, thus, the clamping force of the clamp mechanism 63 is varied.

As shown in FIGS. 11 and 12, the distal end 10 of the transmission light guide assembly 2 is led through the second sleeve 76 and the second cone member 78. Thereafter, the light guide tip assembly 1 and the transmission light guide assembly 2 are connected to one another and the light guide tip assembly 1, which has been inserted partially into the applicator adapter 60, is moved further through the applicator adapter 60 with the distal end 10 of the transmission light guide assembly 2 following. Once the proximal coupling member 4 has been positioned inside the tube 62, in particular in a section between the first cone member 77 and the main part 61, the gear members 83, 84 are engaged with one another, wherein the first and second sleeves 75, 76 are axially moved towards one another until the first and second cone members 77, 78 produce a sufficiently high clamping force applied onto the outside of the cable 15 of the transmission light guide assembly 2. Thus, the axial relative position of the light guide tip assembly 1 with respect to the applicator adapter 60 is adjustable in approximately the range of the pipe 62 between the main part 61 and the first cone member 77. The proximal coupling member 4 is fixed to the applicator adapter 60 indirectly via its connection to the transmission light guide assembly 2, which is fixed by the clamp mechanism 63.

As the inner space 81 of the clamp mechanism 63 is significantly larger than the diameter of the optical fiber 23 of the transmission light guide assembly 2, e.g. ten times larger, the clamp mechanism 63 can be easily and safely sterilized.

The light guide unit 200 of the second embodiment, as shown in FIGS. 11 to 13, does not comprise the tube 18, but it is possible to modify the applicator adapter 60 of the second embodiment such that also the tube 18 of the first embodiment can be accommodated by the applicator adapter, e.g. the internal dimensions of the applicator adapter could be widened accordingly. If desired, also the tube 18 could be adapted to be used in such an applicator adapter, e.g. by omitting the securing section 24 of the tube 18.

Each of the described applicator adapters might also be provided (e.g. sold) without the light guide tip assembly, the transmission light guide assembly and the tube.

In a modification, it is possible to provide the light guide tip assembly with a proximal coupling member that is not cast onto the optical fiber of the light guide tip assembly.

What is claimed is:

1. A light guide unit for a medical laser applicator, the light guide unit comprising:
   a light guide tip assembly removably insertable into the laser applicator, the light guide tip assembly comprising:
   a first optical fiber having an application end and a proximal end; and
   a proximal coupling member provided on the proximal end of the optical fiber, wherein the proximal coupling member is connected to the optical fiber by a cast connection, the proximal coupling member comprising a proximal connector having a cavity;
   a transmission light guide assembly removably insertable into the light guide tip assembly, the transmission light guide assembly comprising:
   a hollow cable;
   a second optical fiber distinct from the first optical fiber and extending through a length of the hollow cable; and a distal connector provided at the distal end of the hollow cable and configured to be inserted into the proximal coupling member of the light guide tip assembly and configured to provide a releasable connection between the first optical fiber and second optical fiber without an imaging optical device between the first optical fiber and second optical fiber; and a tube that at least partially accommodates the light guide tip assembly and the transmission light guide assembly, wherein the tube has an inner dimension corresponding to an outer dimension of the proximal connector of the proximal coupling member in a connected or disconnected state, the outer dimension of the proximal connector increasing during a connecting action that includes insertion of the distal connector into the cavity of the proximal connector.

2. The light guide unit according to claim 1, wherein the light guide tip assembly is sterilized.

3. The light guide unit according to claim 1, wherein the proximal coupling member comprises a proximal connector that can be connected to a corresponding distal connector of a transmission light guide assembly through which light can be transmitted to and/or from the light guide tip assembly.

4. The light guide unit according to claim 1, wherein the proximal coupling member has a fixing portion by means of which the proximal coupling member can be fixed to an applicator adapter.

5. The light guide unit according to claim 1, wherein the tube and the light guide tip assembly are movable relative to one another between a first relative position in which the proximal coupling member is located at a proximal end of the tube, and a second relative position in which the proximal coupling member is located closer to a distal end of the tube, or even at the distal end of the tube.

6. The light guide unit according to claim 1, wherein the tube is sterilized.

7. The light guide unit according to claim 1, wherein the light guide unit further comprises an applicator adapter positioned at the distal end of the tube and by means of which the light guide tip assembly can be secured to the laser applicator, the applicator adapter comprising:

an applicator attachment element by means of which the applicator adapter can be secured to the laser applicator, and an attachment member of the applicator attachment element for securing the transmission light guide assembly to the applicator adapter, wherein light is transmittable to and/or from the light guide tip assembly through the transmission light guide assembly.

8. The light guide unit according to claim 7, wherein the applicator adapter comprises a pipe that can accommodate the proximal coupling member of the light guide tip assembly.

9. The light guide unit according to claim 7, wherein the applicator adapter comprises a pipe that can accommodate a portion of the tube.

10. The light guide unit according to claim 9, wherein the tube can at least partially be position between the pipe and the attachment member.

11. The light guide unit according to claim 7, wherein the attachment member comprises male and female cone members, wherein the male cone member comprises flexible clamp fingers that are varying an inner space of the attachment member surrounded by the flexible clamp fingers when the male cone member is in engagement with the female cone member and is axially moved towards or away from the female cone member.

12. The light guide unit according to claim 11, wherein the applicator adapter has a pipe, a portion of the pipe belonging to the attachment member.

13. The light guide unit according to claim 12, wherein said portion of the pipe comprises one of the cone members.

14. The light guide unit according to claim 12, wherein said portion of the pipe comprises a part of an adjustment drive mechanism, wherein the axial relative position of the cone members can be adjusted by means of the adjustment drive mechanism.

15. The light guide unit according to claim 7, wherein the applicator adapter is sterilized.

16. The light guide unit according to claim 1, wherein the cast connection comprises an injection mold connection, wherein the optical fiber is inserted in the mold.

17. The light guide unit according to claim 1, wherein the proximal connector includes one or more flexible hooks configured to extend outwardly increasing the outer dimension of the proximal connector during the connecting action.

* * * * *